United States Patent [19]

Dorlars et al.

[11] 4,229,579
[45] Oct. 21, 1980

[54] 3-(HALOPYRAZOLYL)-7-TRIAZOLYL-COUMARIN COMPOUNDS

[75] Inventors: Alfons Dorlars, Leverkusen; Carl-Wolfgang Schellhammer, Opladen, both of Fed. Rep. of Germany

[73] Assignee: Bayer Aktiengesellschaft, Leverkusen, Fed. Rep. of Germany

[21] Appl. No.: 896,503

[22] Filed: Apr. 17, 1978

Related U.S. Application Data

[63] Continuation of Ser. No. 167,859, Jul. 30, 1971, abandoned, which is a continuation of Ser. No. 443,722, Feb. 19, 1974, Pat. No. 4,144,243.

[30] Foreign Application Priority Data

Jul. 30, 1970 [DE] Fed. Rep. of Germany ....... 2037854

[51] Int. Cl.² .................... C07D 407/14; C09K 1/02
[52] U.S. Cl. .............................. 548/256; 252/301.29
[58] Field of Search ............... 260/308 A, 308 B; 542/428, 431, 458; 548/256

[56] References Cited

U.S. PATENT DOCUMENTS

| | | | |
|---|---|---|---|
| 3,663,560 | 5/1972 | Schellhammer et al. | 260/308 A |
| 3,784,570 | 1/1974 | Schellhammer | 260/308 A |
| 4,144,243 | 3/1979 | Dorlars et al. | 260/308 A |

FOREIGN PATENT DOCUMENTS 2000071  8/1969  France .......................... 260/308 A

OTHER PUBLICATIONS

Soap & Chemical Specialties, vol. 43, pp. 84, 86, 90, 92, 130, 132, 134 (1967).
Ganz, Applied Optics, vol. 15, pp. 2039–2058 (1976).
Thielert I, J. Opt. Soc. America, vol. 12, pp. 1607–1612 (1973).
Thielert II, Die Farbe, vol. 21, pp. 113–130 (1972).
Berger, Die Farbe, vol. 8, pp. 187–202 (1959).

*Primary Examiner*—Alton D. Rollins
*Attorney, Agent, or Firm*—Sprung, Felfe, Horn, Lynch & Kramer

[57] ABSTRACT

Coumarine compounds of the formula

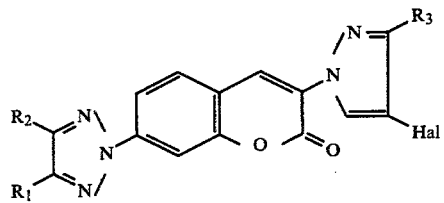

in which
  $R_1$ and $R_2$ denote hydrogen, alkyl, cycloalkyl, aralkyl, aryl, nitrile, carboxyl, carboxylic acid ester or carboxylic acid amide groups, or together form a nonaromatic 5-membered or 6-membered ring system,
  $R_3$ represents hydrogen, or alkyl or aryl radicals and Hal represents bromine or preferably chlorine as well as their production and use as optical brighteners.

7 Claims, No Drawings

3-(HALOPYRAZOLYL)-7-TRIAZOLYL-COUMARIN COMPOUNDS

This is a Continuation, of application Ser. No. 167,859, filed July 30, 1971, abandoned, and Ser. No. 443,722, filed Feb. 19, 1974, now U.S. Pat. No. 4,144,243.

The subject of the present invention are coumarine compounds of the formula

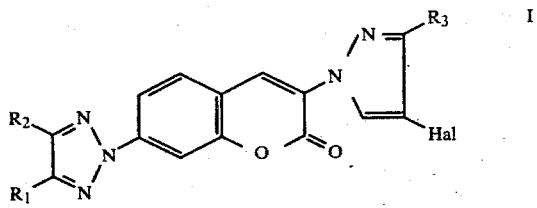

in which
$R_1$ and $R_2$ denote hydrogen, alkyl, cycloalkyl, aralkyl, aryl, nitrile, carboxyl, carboxylic acid ester or carboxylic acid amide groups, or together form a non-aromatic 5-membered or 6-membered ring system,
$R_3$ represents hydrogen, or alkyl or aryl radicals, and Hal represents bromine or preferably chlorine, as well as their manufacture and use as optical brighteners.

By the alkyl radicals $R_1$, $R_2$ and $R_3$, there are to be understood straight-chain or branched, saturated or unsaturated alkyl groups with 1-4 C atoms which can be substituted by substituents such as halogen atoms, for example fluorine, chlorine and bromine, hydroxyl groups, alkoxy groups with 1-4 C atoms, alkylcarbonyloxy groups with 1-4 C atoms in the alkyl radical, carboxylic acid groups and alkoxycarbonyl groups with 1-4 C atoms in the alkyl radical.

Suitable alkyl radicals $R_1$ to $R_3$ are, for example; methyl, ethyl, β-hydroxyethyl, β-acetoxyethyl, β-chloroethyl, carboxyethyl, carboethoxyethyl, ethoxyethyl, n- and isopropyl, n-, iso- and tert.-butyl, isobutenyl, pentyl, hexyl, octyl, isooctyl, nonyl, decyl and dodecyl.

By the aryl radicals $R_1$ to $R_3$, there are especially to be understood phenyl radicals which can carry one or more substituents, for example fluorine, chlorine, bromine, nitrile, alkyl and alkoxy groups with 1-4 C atoms, the carboxyl group, alkoxycarbonyl groups with 2-5 C atoms, alkylsulphonyl groups with 1-4 C atoms, phenyl radicals, sulphonic acid groups (including their salts), sulphonamide groups which are optionally substituted by lower alkyl radicals, and sulphonic acid ester groups.

Examples of such radicals are the following: phenyl, o-, m- and p-fluorophenyl, o-, m- and p-chlorophenyl, o-, m- and p-bromophenyl, o-, m- and p-ethoxycarbonylphenyl, m- and p-methanesulphonylphenyl, m- and p-ethanesulphonylphenyl, p-benzylphenyl, p-benzyloxyphenyl and p-biphenyl radicals.

Suitable cycloalkyl radicals $R_1$ and $R_2$ are especially cyclopentyl and cyclohexyl radicals.

Suitable aralkyl radicals $R_1$ and $R_2$ are, above all, benzyl, p-chlorobenzyl, β-phenylethyl and styryl radicals.

Non-aromatic ring systems fused to the triazole ring, which $R_1$ and $R_2$ together with the two C atoms of the triazole ring can furthermore symbolise, are especilly cyclopentane and cyclohexane rings, which can in turn be further fused to a benzene ring. As examples of these fused systems, the following may be singled out:

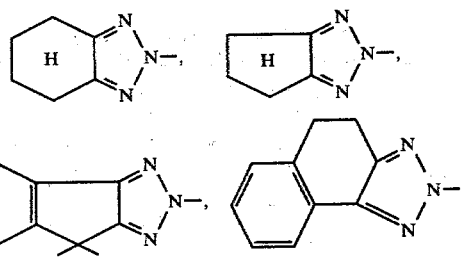

Suitable carboxylic acid ester groups $R_1$ and $R_2$ are especially alkoxycarbonyl groups with 1-4 C atoms in the alkoxy groups, such as methoxycarbonyl radicals or butoxycarbonyl radicals.

Suitable carboxylic acid amide groups $R_1$ and $R_2$ are carboxylic acid amide groups which are optionally monosubstituted or disubstituted by alkyl radicals with 1-4 C atoms. The groups $—CONH_2$, $—CONHCH_3$, $—CONHC_4H_9$, $—CON(CH_3)_2$ and $—CON(C_4H_9)_2$ may be mentioned as examples.

Particularly preferred coumarine compounds within the framework of the formula I are those of the formula

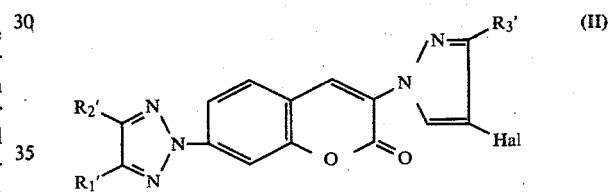

in which
$R'_1$, $R'_2$ and $R'_3$ represent hydrogen, alkyl radicals which are optionally substituted by halogen, hydroxyl alkoxy, alkylcarbonyloxy, carboxyl or alkoxycarbonyl groups, or phenyl radicals which are optionally substituted by halogen, nitrile, alkyl, alkoxy, carboxyl, alkoxycarbonyl, alkylsulphonyl, phenyl, sulphonic acid, sulphonamide which is optionally substituted by alkyl radicals, or sulphonic acid ester groups; and
$R'_1$ and $R'_2$ furthermore denote cyclohexyl, benzyl or phenylethyl radicals, or form the remaining members of a fused cyclohexyl or cyclopentyl radical, in which the alkyl radicals and alkoxy radicals preferably contain 1-4 C atoms and
Hal has the abovementioned meaning.

Suitable brighteners within the framework of the formula I are, furthermore, those compounds of the formula

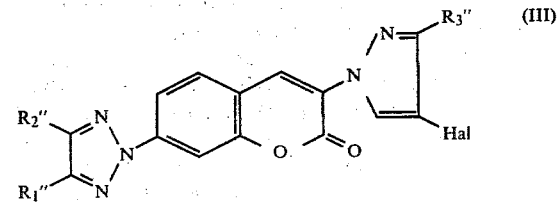

in which

R″₂ represents a nitrile, carboxyl, carboxylic acid ester or carbonamide group,

R″₁ and R″₃ have the same meaning as R′₁ and R′₃, and

Hal represents bromine or, preferably, chlorine.

The new brighteners of the formula I are obtained if coumarine compounds of the formula

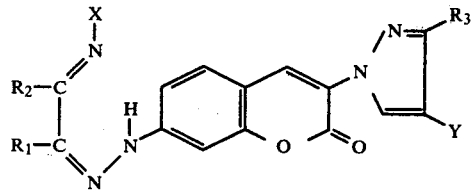

in which

R₁, R₂ and R₃ have the abovementioned meaning,

X represents hydrogen or hydroxyl and

Y denotes chlorine, bromine or hydrogen, are cyclised, with elimination of HX, by treatment with dehydrogenating agents or dehydrating agents at elevated temperatures—optionally in an inert solvent— —and are subsequently chlorinated or brominated in the case where Y represents hydrogen.

Those coumarine compounds which possess the formula II within the framework of the compounds of the formula I are appropriately obtained by triazolizing compounds of the formula

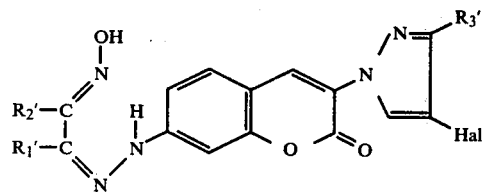

in which

R′₁, R′₂, R′₃ and Hal have the abovementioned meaning, either directly by treatment with dehydrating agents or by the action of dehydrogenating agents, firstly to give the corresponding triazole-N-oxides of the formula

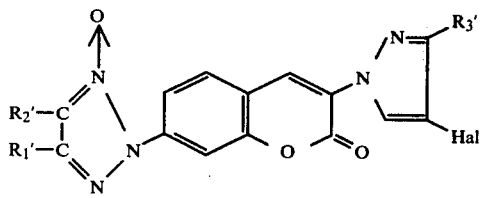

in which

R′₁, R′₂, R′₃ and Hal have the abovementioned meaning, and subsequently reducing these.

The dehydration of the coumarine compounds IV or V takes place in a manner which is in itself known, by heating with agents which eliminate water, such as acid anhydrides and acid halides.

As examples of these, there may be mentioned: acetic anhydride, propionic anhydride, acetyl chloride, thionyl chloride, sulphuryl chloride, and phosphorus pentoxide, amongst which acetic anhydride is to be regarded as particularly suitable; it is employed either in a copious excess or in conjunction with solvents.

Suitable solvents are dimethylsulphoxide, dimethylformamide, N-methylpyrrolidone, tetramethylurea, o-dichlorobenzene and others. In most cases it is desirable to add bases, such as lithium acetate, sodium acetate or potassium acetate, trimethylamine, triethylamine, dimethylbenzylamine, pyridine or higher pyridine homologues.

The temperatures at which the dehydration is carried out can be varied within a substantial range. In general, temperatures between 40° and 160° C., preferably between 60° and 140° C., are used.

The cyclisation of the compounds V to give the triazole-N-oxides of the formula VI in the presence of dehydrogenating agents is appropriately carried out in those solvents which are inert under the reaction conditions used and towards the particular oxidising agents chosen, such as, for example, pyridine, higher pyridine bases, dimethylformamide, N-methylpyrrolidone, dimethylsulphoxide, acetic acid and their mixtures with water.

Suitable dehydrogenating agents are, amongst others, mercuric oxide, cupric salts, such as copper acetate and copper sulphate, complex cupric salts, lead dioxide, lead tetraacetate, sodium bichromate and potassium bichromate, potassium ferricyanide, hydrogen peroxide, peracetic acid and potassium peroxy disulphate.

An industrially preferred embodiment consists of the dehydrogenation of compounds of the formula V in pyridine or technical pyridine bases, with cupric salts such as copper acetate or copper sulphate, which can be used in the solid form or in aqueous solution; it may be appropriate to blow in air.

This oxidative cyclisation is in general carried out at temperatures of about 0° C. to 100° C., preferably of 20° to 80° C.

The subsequent reduction of the triazole-N-oxides VI can for example be effected by zinc dust and zinc amalgam in a solution or suspension containing acetic acid or a mineral acid, or by tin granules or stannous chloride in mineral acids.

The coumarines of the formula (V) required as starting substances can be manufactured in a manner which is in itself known, by condensing 4-acetamino-2-hydroxybenzaldehyde or its anil with pyrazolylacetic acids of the formula

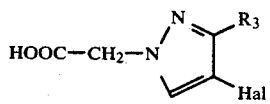

wherein

R₃ and Hal have the abovementioned meaning, to give 7-acetamino-3-[chloro-pyrazolyl-(1)]-coumarines, subsequently hydrolysing the acetamino group to the amino group, converting the 7-aminocoumarines obtained, by diazotisation and subsequent reduction, into the corresponding 7-hydrazinocoumarines, and finally condensing these, again in a manner which is in itself known, with α-oximinoketones of the formula

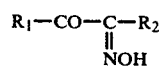

to give the oximinohydrazones of the formula V.

The pyrazolylacetic acids are in part known. They are obtained in a manner which is in itself known (compare German Patent Application P 19 42 926.6) by chlorination or bromination of the corresponding halogen-free pyrazolacetic acids.

Suitable pyrazolacetic acids (VII) are, for example: 4-chloropyrazolyl-(1)-acetic acid, 3-methyl-4-chloropyrazolyl-(1)-acetic acid, 3-phenyl-4-chloropyrazolyl-(1)-acetic acid, 3-p-tolyl-4-chloropyrazolyl-(1)-acetic acid, 3-p-anisyl-4-chlorpyrazolyl-(1)-acetic acid, 3-p-chlorophenyl-4-chloropyrazolyl-(1)-acetic acid, 3-ethyl-4-chloropyrazolyl-(1)-acetic acid, 3-propyl-4-chloropyrazolyl-(1)-acetic acid and 4-bromopyrazolyl-(1)-acetic acid.

Suitable compounds (VIII) are, amongst others: oximinoacetone, diacetylmonoxime, 1-oximino-butanone-(2), 2-oximino-1-phenyl-butanone-(3), 1,3-diphenyl-1-oximinopropanone-(2), oximinobenzyl-cyclohexyl-ketone, 1-oximino-4-phenyl-buten-(3)-one-(2), 2-oximino-pentanone-(3), 3-oximino-4-methyl-pentanone-(2), 1-oximino-4-methylpenten-(3)-one-(2), 3-oximino-pentanol-(5)-one-(2), 3-oximinohexanone-(2), 2-oximino-5-methyl-hexanone-(3), 2-oximino-heptanone-(3), 3-oximino-heptanone-(4), 3-oximino-octanone-(2), 4-oximino-nonanone-(5), 3-oximino-5-äthyl-nonanon-(2), 9-oximinononadecanone-(10), oximinoacetophene, p-fluoro-, p-chloro- and p-bromo-oximinoacetophenone, p-methyl- and p-methoxyoximinoacetophenone, 2,4- and 3,4-dimethyl-oximinoacetophenone, oximino-propiophenone, p-fluoro-, p-chloro- and p-bromooximinopropiophenone, p-methyl-, p-benzyl-, p-dimethylbenzyl, p-ethyl-, p-isopropyl-, p-tert.-butyl and p-phenyl-oximinopropiophenone, p-methoxy- and p-ethoxy-oximinopropiophenone, p-benzyloxyoximino propiophenone, 2,5-dimethyl-oximinopropiophenone, 2-oximino-1,3-diphenylpropanone-(1), 1-oximino-1-phenylacetone, 1-oximino-1-o-, -m- and -p-tolylacetone, 1-oximino-1-o-, -m-, and -p-anisylacetone, 1-oximino-1-o-, -m- and -p-chlorophenylacetone, 1-oximino-1-m- and -p-cyanophenyl-acetone, 1-oximino-1-m- and -p-carboethoxyphenyl-acetone, 1-oximino-1-m- and p-methanesulphonylphenyl-acetone, 1-oximino-1,3-diphenylacetone, oximinobutyrophenone, γ-benzoyl-γ-oximino-butyric acid methyl ester and ethyl ester, oximinovalerophenone, oximino-1- and -2-propionaphthone, benzilmonoxime, tolilmonoxime, anisilmonoxime, oximinocyclopentanone, oximinocyclohexanone, 2-oximino-indanone-(1), and 2-oximino-tetralone-(1).

The coumarine compounds which correspond to the formula III are advantageously manufactured by triazolizing compounds of the formula

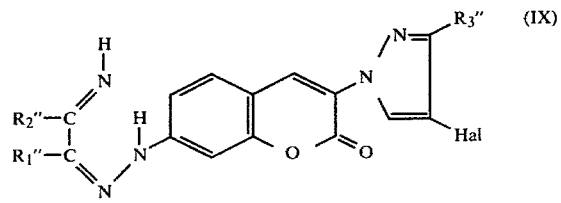

in which

R"$_1$, R"$_2$, R"$_3$ and Hal have the abovementioned meaning, by treatment with dehydrogenating agents.

A preferred embodiment of this dehydrogenation is characterized in that the compounds IX are first converted into the copper complexes with the aid of cupric salts, and that these are converted into the corresponding 7-triazolylcoumarine compounds by warming in the presence of excess complex cupric salt solution.

Further, lead tetraacetate is for example suitable for use as a dehydrogenating agent.

The coumarine compounds of the formula IX required as starting compounds are for example obtainable by diazotising 7-aminocoumarine derivatives of the formula

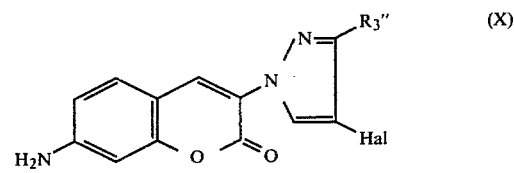

wherein

R$_3$ and Hal have the abovementioned meaning, and coupling the products with enamines of the formula

wherein

R$_1$ and R$_2$ have the abovementioned meaning.

The subsequent halogenation of the pyrazole ring of the pyrazolylcoumarine compounds—obtained by cyclisation of the compounds IV (Y=H) - of the formula

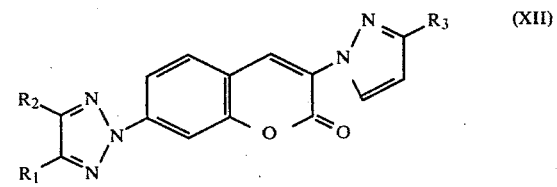

wherein

R$_1$, R$_2$ and R$_3$ have the initially mentioned meaning, can be effected according to methods which are in themselves known, for example with elementary chlorine or bromine in glacial acetic acid, with hypochlorite or hypobromite in glacial acetic acid, or with sulphuryl chloride or phosphorus pentachloride in non-polar solvents, especially in chlorinated hydrocarbon such as dichloroethane, trichloroethane and tetrachloroethane and monochlorobenzene, dichlorobenzene and trichlorobenzene and their mixtures.

The substituents of the new coumarine compounds of the formulae I to III, obtainable according to one of the above-mentioned processes, can of course, subsequent to the complete synthesis, be converted further in a manner which is in itself known.

Thus, for example, sulphonic acid groups can be introduced into aryl radicals R$_1$ to R$_3$ by subsequent sulphonation, or sulphonic acid groups present can be converted in a known manner into sulphonamide and sulphonic acid ester groups.

Furthermore, for example, nitrile groups can be converted into carboxyl, carbonamide or carboxylic acid ester groups, and carboxyl groups can be esterified or amidised.

The new coumarine compounds of the formula (I) are valuable brighteners. They are suitable for brightening the most diverse materials, especially for brightening fibres, filaments, woven fabrics, knitted fabrics and films of synthetic origin, above all for brightening materials made from polyesters, polyurethanes, polycarbonates, polyvinyl chloride and polyamide, as well as for brightening lacquers made from cellulose esters and nitrocellulose. The compounds (I) containing sulphonic acid groups are furthermore suitable for brightening natural materials such as wool, silk and cellulose, as well as regenerated cellulose and cellulose acetates. They can be employed in the usual manner, for example in the form of aqueous dispersions or solutions, or in the form of solutions in inert solvents; if desired, they can also be used in combination with detergents or added to casting compositions which are used for the manufacture of films or filaments. Because of their high stability, they can, for example, also already be added to polyesters during their manufacture from the components; they can be added to polycondensates after the pre-condensation or during the polycondensation. The amounts of pyrazolyl-triazolyl-coumarines required in each case can be easily determined by preliminary experiments; in general, amounts of 0.01–1%, relative to the weight of the material to be treated, suffice. The pyrazolyl-triazolyl-coumarines of the formula I are very high-yield brighteners; the brightening effects achieved are very light-fast and in general show excellent fastness to washing.

Coumarine compounds of the general formula I which contain one or more alkyl radicals with 4–12 C atoms are in many cases suitable for optically brightening synthetic fibre materials from organic solvents. The process is characterised in that the fibre materials are impregnated with dyeing liquors which contain these brighteners, and are subsequently subjected to a heat treatment.

As compared to the 3-pyrazolyl-7-benzo- and -naphthotriazolyl-coumarines described in Belgian Patent Specification No. 681,962, the new coumarine derivatives of the formula (I), substituted by monocyclic triazolyl-(2) radicals, show considerably improved affinity for polyester materials; as compared to the 3-aryl-7-triazolyl-(2)-coumarines described in Belgian Patent Specification No. 695,656, and also as compared to the coumarine compounds described in the first-mentioned Belgian Patent Specification, the chloropyrazolyl-triazolyl-(2)-coumarines of the formula (I) are distinguished by stronger, clearer and more brilliant brightening effects in the thermosol treatment of polyester materials.

As compared to the pyrazolyl-v-triazolylcoumarines of Belgian Patent Specification No. 726,619 which have the nearest comparable structure, the present compounds of the formula I are distinguished by improved resistance to chlorine and to chlorite.

EXAMPLE 1

Manufacture of
3-[4-chloropyrazolyl-(1)]-7-[4-phenyl-5-methyl-v-triazolyl-(2)]-coumarine (1 h)

1.14 kg of pyrazolyl-(1)-acetic acid are stirred with 6 liters of concentrated hydrochloric acid. A solution of 324 g of sodium chlorate in 1.35 kg of water is added dropwise at 30° C. below the surface, and the mixture is then stirred for a further 30 minutes. The mixture is diluted to 18 liters with ice, and the material which separates out is filtered off. After washing the filter cake until neutral, and drying it at 120° C., 1.068 kg of 4-chloro-pyrazolyl-(1)-acetic acid of melting point 160° C. are obtained.

2.04 kg of acetic anhydride, 1.016 kg of 4-acetylaminosalicylidene-aniline, 0.41 kg of anhydrous sodium acetate and 0.803 kg of 4-chloro-pyrazolyl-(1)-acetic acid are heated to 145° C. for 15 hours. The temperature of the mixture is allowed to drop to 90° C., 4 kg of ice are added to the melt, and the 7-acetylamino-3-[4-chloro-pyrazolyl-(1)]-coumarine which has separated out after cooling to 20° C. is filtered off. The filter cake is washed with 4 kg of acetone. After drying, 0.847 kg of 7-acetylamino-3-[4-chloro-pyrazolyl-(1)]-coumarine is obtained in the form of brownish small crystals of melting point 288°–290° C.

92 g of 7-acetylamino-3-[4-chloro-pyrazolyl-(1)]-coumarine in 180 ml of 78% strength sulphuric acid are stirred for 1 hour at 100° C. The mixture is then cooled to 20° C., 600 ml of glacial acetic acid are added, and the substance diazotised at +16° C. with a solution of 21 g of sodium nitrite in 100 ml of water. After 3 hours, the diazonium salt solution is cooled to 0° C., and a solution of 136 g of stannous chloride in 300 ml of concentrated hydrochloric acid is added. After one hour, the yellow material which has separated out is filtered off and suspended in 2 liters of water, and the suspension is rendered ammoniacal. After filtering off, washing with water and drying, 93 g of 7-hydrazino-3-[4-chloropyrazolyl-(1)]-coumarine of melting point 209° C. (decomposition) are obtained.

93 g of 7-hydrazino-3-[4-chlorpyrazolyl-(1)]-coumarine are stirred for 12 hours at 95° C. with 60 g of oximinopropiophenone and 10 ml of 50% strength acetic acid in 220 ml of methylglycol. The bronze-coloured crystals which have separated out after cooling to 5° C. are filtered off, washed with 200 ml of methanol and dried. 133 g of oximinopropiophenone-[3-(4-chloro-pyrazolyl)-coumarinyl-(7)]-hydrazone are obtained in the form of bronze-coloured to yellow crystals of melting point 274°–275° C. (decomposition). 133 g of oximinopropiophenone-[3-(4-chloropyrazolyl)-coumarinyl-(7)]-hydrazone in 230 ml of pyridine are treated dropwise with 40 g of acetic anhydride whilst stirring and keeping the temperature at 85° to 90° C. After stirring for three hours at 85° to 95° C., the pasty reaction mixture is cooled to 10° C. and the light crystals which have separated out are filtered off. They are rinsed with 100 ml of methanol, then with ½ l of warm 8% strength hydrochloric acid, and finally with 1 l of water. After drying, 125 g of a light grey crystal powder are obtained, and this is purified by boiling it together with 95 g of fuller's earth in 1.2 l of chlorobenzene for 1 hour. Finally, the chlorobenzene solution is clarified by passing it through a prewarmed pressure filter, the filtrate is cooled to approx. 0° and after standing for several hours the crystals which have separated out are filtered off, washed with 200 ml of cold methanol and dried. 113 g of 3-[4-chloropyrazolyl-(1)]-7-[4-phenyl-5-methyl-v-triazlyl-(2)]-coumarine are obtained as greenish-tinged light yellow crystals, which give a colourless solution in dimethylformamide; this solution fluoresces intensely violet-tinged blue on irradiation with UV light of 350 mµ.

The compounds of the formula (I) listed under a - t in the Table below were manufactured analogously from 7-hydrazino-3-chloropyrazolyl-coumarine and the corresponding α-oximinoketones; the compounds u and v were prepared starting from 7-hydrazino-3-[3-methylor -phenyl-4-chloro-pyrazolyl-(1)]-coumarine and the oximinoketones mentioned.

| No. | R₁ | R₂ | R₃ | α-Oximinoketone | Colour of fluorescence in DMF (350 mµ) |
|---|---|---|---|---|---|
| 1a | H | CH₃ | H | oximinoacetone | strong reddish-tinged blue fluorescence |
| 1b | C₂H₅ | CH₃ | H | 2-oximinopentanone-(3) | " |
| 1c | n-C₃H₇ | C₂H₅ | H | 3-oximinoheptanone-(4) | " |
| 1d | CH₃ | —CH(CH₃)₂ | H | 2-methyl-3-oximino-pentanone-(4) | " |
| 1e | CH₃ | n-C₁₀H₂₁ | H | 3-oximinotridecanone-(2) | " |
| 1f | CH₃ | —CH₂— | H | 2-oximino-1-phenylbutanone-(3) | strong somewhat reddish-tinged blue fluorescence |
| 1g |  | H | H | oximinoacetophenone | strong somewhat reddish-tinged blue fluorescence |
| 1h |  | CH₃ | H | oximinopropiophenone | strong somewhat reddish-tinged blue fluorescence |
| 1i | CH₃ |  | H | 1-oximino-1-phenylacetone | strong somewhat reddish-tinged blue fluorescence |
| 1k | CH₃ |  | H | 4-chloro-oximinopropiophenone | strong somewhat reddish-tinged blue fluorescence |
| 1l | CH₃ | 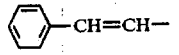 | H | 1-m-cyanophenyl-1-oximino-acetone | strong somewhat reddish-tinged blue fluorescence |
| 1m | 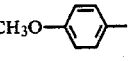 —CH=CH— | H | H | oximino-benzalacetone | strong somewhat reddish-tinged blue fluorescence |
| 1n | (CH₃)₃C— | H | H | oximinomethyl-tert.-butyl-ketone | strong reddish-tinged blue fluorescence |
| 1o | CH₃O—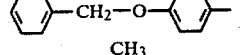 | CH₃ | H | p-methoxy-oximinopropiophenone | blue fluorescence |
| 1p | —CH₂—O—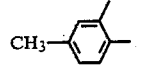 | CH₃ | H | p-benzyloxy-omino-propiophenone | blue fluorescence |
| 1q | 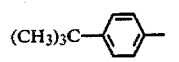 | CH₃ | H | 2,4-dimethyl-oximino-propiophenone | strong reddish-tinged blue fluorescence |
| 1r | (CH₃)₃C—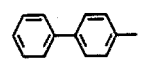 | CH₃ | H | 4-tert.-butyl-oximino-propiophenone | strong reddish-tinged blue fluorescence |
| 1s | 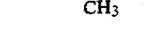 | CH₃ | H | 4-phenyl-oximinopropio-phenone | strong blue fluorescence |
| 1t | 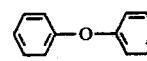—O—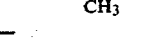 | CH₃ | H | 4-phenoxy-oximinopropio-phenone | strong blue fluorescence |
| 1u | CH₃ | 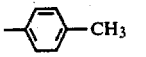—CH₃ | H | 1-p-tolyl-1-oximino-acetone | strong somewhat reddish-tinged blue fluorescence |
| 1v | F— | H | H | 4-fluoro-oximino-acetophenone | strong somewhat reddish-tinged blue fluorescence |
| 1w | —CH₂ | 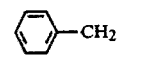 | H | 1-oximino-1,3-diphenyl-acetone or 2-oximino-1,3-diphenylpropanone | strong blue fluorescence |
| 1x |  |  | H | benzilmonixime | " |
| 1y |  | C₃H₇ | H | oximinovalerophenone | strong somewhat reddish-tinged blue fluorescence |
| 1z | 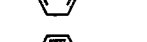 | 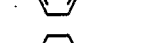 | H | oximinobenzyl-cyclohexyl-ketone | strong somewhat reddish-tinged blue fluorescence |

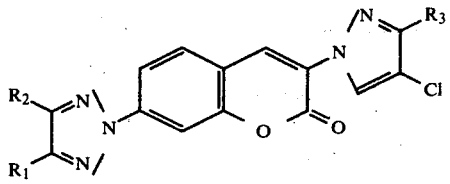

| No. | R₁ | R₂ | R₃ | α-Oximinoketone | Colour of fluorescence in DMF (350 mµ) |
|---|---|---|---|---|---|
| a₁ | C₆H₅—CH₂—C₆H₅ | CH₃ | H | p-benzyl-oximinopropiophenone | " |
| a₂ | (o-CH₂-phenyl) | | H | 2-oximinoindanone-(1) | strong blue fluorescence |
| a₃ | $C_2H_5$ | $CH_3$ | $CH_3$ | 2-oximinopentanone-(3) | strong slightly reddish-tinged blue fluorescence |
| a₄ | $C_2H_5$ | $CH_3$ | (phenyl) | 2-oximinopentanone-(3) | " |
| a₅ | (phenyl) | $C_2H_5$ | H | oximinobutyrophenone | strong somewhat reddish-tinged blue fluorescence |

EXAMPLE a₆

16.1 g of 3-[pyrazolyl-(1)]-7-[4-ethyl-5-methyl-v-triazolyl-(2)]-coumarine (compare Belgian Patent Specification No. 726,619, Example 1 d) are dissolved in 600 ml of warm glacial acetic acid and treated with 10 g of bromine at approx. 40° C. After standing for 3 hours at 45°–50° C., half the glacial acetic acid is distilled off under reduced pressure and the yellow crystals which separate out on cooling are filtered off and recrystallised from chlorobenzene. 18 g of 3-[4-bromopyrazolyl-(1)]-7-[4-ethyl-5-methyl-v-triazolyl-(2)]-coumarine are obtained as light greenish-tinged crystals (F. 189°–190°) which dissolve in dimethylformamide to give a strong reddish-tinged blue fluorescence.

EXAMPLE a₇

3-[Pyrazolyl-(1)]-7-[4-phenyl-5-methyl-v-triazolyl-(2)]-coumarine (compare Belgian Patent Specification No. 726,619, Example 1 a) can analogously be reacted with bromine, in glacial acetic acid, to give 3-[4-bromopyrazolyl-(1)]-7-[4-phenyl-5-methyl-v-triazolyl-(1)]-coumarine, which after recrystallisation from dimethylformamide is in the form of greenish-tinged light needles and gives a strong reddish-tinged blue fluorescence in dimethylformamide solution.

EXAMPLE 2

(a) 27 g of 7-amino-3-[4-chloropyrazolyl-(1)]-coumarine in a mixture of 300 ml of glacial acetic acid and 25 ml of concentrated hydrochloric acid are diazotised with 7 g of sodium nitrite in 25 ml of water, at 0°–5° C. The resulting diazo suspension is run dropwise, at approx. 10°–15° C., into a solution of 16 g of β-aminocinnamic acid nitrile in 200 ml of 80% strength alcohol, whilst constantly maintaining a pH value of 5–6 by adding aqueous sodium acetate solution. After completion of the coupling, the orange-brown azo compound is filtered off, washed with water and dried.

40 g of the azo dyestuff thus obtained are stirred in 320 ml of pyridine, and 38 g of cupric acetate are gradually added at 50° C. The mixture is stirred for a further 6 hours at 50° C. and 1 hour at 75° C., thereafter the bulk of the pyridine is stripped off in vacuo, and the residue is treated with 300 ml of 60% strength aqueous methanol. The precipitate formed is filtered off whilst still hot, dried and extracted with chlorobenzene. The crude product which remains after evaporating off the extraction agent is purified by recrystallisation from glycol monomethyl ether and subsequently from dimethylformamide. The crystalline product is filtered off, washed with cold methanol and dried. 29.5 g of greenish-white crystals of 3-[4-chloropyrazolyl-(1)]-7-[4-phenyl-5-cyano-v-triazolyl-(2)]-coumarine are obtained, and this substance gives a colourless solution in dimethylformamide; this solution fluoresces reddish-tinged blue on irradiation with UV light of 350 mµ.

The chloropyrazolyl-v-triazolyl-coumarine compounds listed in the Table below were manufactured analogously from 7-amino-3-[4-chloropyrazolyl-(1)]-coumarine (a-e) or 7-amino-3-[3-phenyl-4-chloropyrazolyl-(1)]-coumarine (f), respectively.

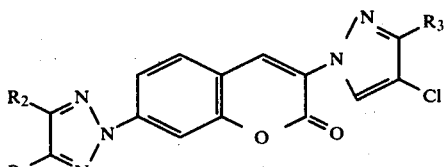

| No. | R₁ | R₂ | R₃ | Manufactured from | Colour of fluorescence in DMF (350 mµ) |
|---|---|---|---|---|---|
| 2b | (phenyl) | COOH | H | β-aminocinnamic acid nitrile, saponified | somewhat reddish-tinged blue fluorescence |

-continued

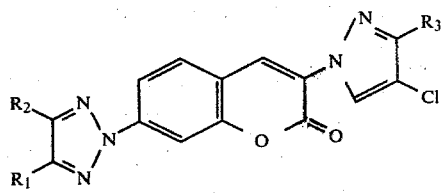

| No. | $R_1$ | $R_2$ | $R_3$ | Manufactured from | Colour of fluorescence in DMF (350 mµ) |
|---|---|---|---|---|---|
| 2c | phenyl | COOC$_2$H$_5$ | H | β-aminocinnamic acid ethyl ester | " |
| 2d | CH$_3$ | COOC$_2$H$_5$ | H | β-aminocrotonic acid ethyl ester | violet-blue fluorescence |
| 2e | phenyl | CONH$_2$ | H | β-aminocinnamic acid amide | blue fluorescence |
| 2f | CH$_3$ | COOC$_2$H$_5$ | phenyl | β-aminocrotonic acid ethyl ester | somewhat reddish-tinged blue fluorescence |

EXAMPLE 3

A woven fabric of polyester fibres is introduced, using a liquor ratio of 1:40, into a bath which per liter contains 1.5 g of sodium oleylsulphonate, 0.75 g of formic acid and 0.1 g of 3-[4-chloropyrazolyl-(1)]-7-[4-phenyl-5-methyl-v-triazolyl-(2)]-coumarine, the manufacture of which is described in Example 1. The bath is heated to the boil over the course of 30 minutes and is kept at the boil for about 45 minutes, whilst moderately agitating the fabric. Thereafter the fabric is rinsed and dried. It then possesses an outstandingly brilliant and strong brightening effect of excellent fastness to light, washing and chlorite.

The brightening effect thus obtained is stronger and clearer than the brightening effect achieved in the same manner with the nearest comparable 3-[pyrazolyl-(1)]-7-naphthotriazolyl-coumarine, described in Belgian Patent Specification No. 681,962, and shows increased stability to bleaching agents containing chlorine, when compared with the pyrazolyl-triazolyl-coumarines of Belgian Patent Specification No. 726,619.

EXAMPLE 4

A fabric of polyester fibres is padded with an aqueous liquor which per liter contains 1 g of one of the compounds listed in Examples 1 or 2 and 3 g of a commercially available dispersing agent based on fatty alcohol polyglycol ethers. The fabric is then squeezed out to a weight increase of 100%, subsequently dried, and heated to 125° C. for 30 minutes. As compared to untreated material, the fabric treated in this way shows a strong clear brightening effect of high fastness to light, wet processing and chlorite.

EXAMPLE 5

A fabric of polyester fibres is padded with an aqueous liquor which per liter contains 1 g of a commercially available dispersing agent based on fatty alcohol polyglycol ethers, 1 g of a commercially available wetting agent based on alkylnaphthalenesulphonic acids, 4 g of alginate thickener and a solution of 1 g of one of the compounds listed in Examples 1 or 2, in 20 g of triethanolamine. The fabric is then squeezed out to a weight increase of 100%, thereafter dried, heated for 1 minute to 190° C. and subsequently washed hot. Compared to untreated fabric, it shows a very strong and brilliant brightening effect of excellent fastness to light, washing and chlorite.

Relative to the nearest comparable phenyl-triazolyl-coumarines, described in Belgian Patent Specification No. 695,656, the pyrazolyl-triazolyl-coumarines according to the invention show stronger and clearer brightening effects; for example, 3-[4-chloropyrazolyl-(1)]-7-[4-phenyl- or -4-p-chlorophenyl-5-methyl-v-triazolyl-(2)]-coumarine Example 1h or 1k) in this way yields stronger and more brilliant brightening effects than does the corresponding 3-phenyl-7-[4-phenyl- or -4-p-chlorophenyl-5-methyl-v-triazolyl-(2)]-coumarine (Belgian Patent Specification No. 695,656, Example 1c or 1d). As compared to the analogous pyrazolyl-v-triazolylcoumarine compounds of Belgian Patent Specification No. 726,619 (Example 1a or 1p), the present chloropyrazolyl-v-triazolylcoumarine compounds show improved stability to bleaching agents containing chlorine under severe conditions.

EXAMPLE 6

6 kg of terephthalic acid dimethyl ester and 5 l of ethylene glycol are mixed with 0.05% of zinc acetate and 0.03% (relative to terephthalic acid dimethyl ester) of one of the compounds listed in Examples 1 to 2a, of the formula I, in a 20 l stirred autoclave. The autoclave is firstly heated to 180° C. whilst stirring. The trans-esterification starts at about 150° C.; the methanol eliminated is distilled off.

After 1 hour the temperature is raised to 200° C. and after a further 45 minutes to 220° C. After a total of 2¾ hours, the trans-esterification is complete. The total amount of methanol split off is at least 2.4 l.

The product thus obtained is transferred under nitrogen into an autoclave, heated to 275° C., for pre-condensation. During the pre-condensation, the excess glycol is directly passed over a condenser and collected. After 45 minutes a slight vacuum is first applied, and this is intensified to (below) 1 mm Hg over the course of a further 45 minutes. The speed of stirring is reduced. After 2½ hours the polycondensation is complete. The product obtained is subsequently spun in a known manner to give filaments of final gauge 50-25 den. The filaments obtained show an excellent brightening effect, with excellent fastness to light and to wet processing.

EXAMPLE 7

Polyamide 6 yarn is treated for 30 minutes, using a liquor ratio of 1:40, in an aqueous bath at 80°–90° C. which per liter contains 0.15 g of the brightener of the formula

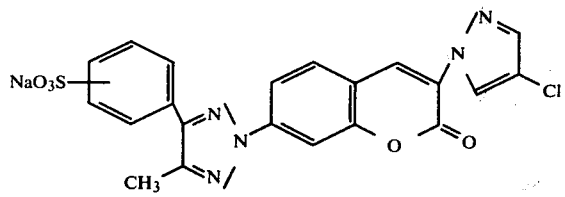

and 2 g of sodium chlorite. After rinsing and drying, the yarn shows a very clear brightening effect of good fastness to light.

The brightener used was manufactured as follows: 10 g of 3-[4-chloropyrazolyl-(1)]-7-[4-phenyl-5-methyl-v-triazolyl-(2)]-coumarine (Example 1) in 85 ml of concentrated sulphuric acid are kept for 2 hours at 115° C., whilst stirring. After cooling, the batch is poured into 400 ml of cold water, sodium chloride is added until precipitation is complete, and the sulphonic acid which has separated out is filtered off. The filter residue is stirred with 500 ml of hot water and neutralised with sodium hydroxide solution. The hot solution is clarified, using adsorbent charcoal, and the sodium sulphonate salt is salted out by adding sodium chloride. The product which has separated out is filtered off, washed with cold 5% sodium chloride solution and dried. The sodium salt of 3-[4-chloropyrazolyl-(1)]-7-[4-sulphophenyl-5-methyl-v-triazolyl-(2)]-coumarine is obtained as a light greenish-tinged crystal powder (yield 10.2 g), of which a colourless solution in dimethylformamide shows a strong violet-tinged blue fluorescence in UV light.

EXAMPLE 8

A fabric of cellulose acetate fibres is agitated for 45 minutes, using a liquor ratio of 1:40, in an aqueous bath at 60° C. which per liter contains 1 g of sodium oleylsulphonate, 0.75 g of formic acid and 0.1 g of one of the compounds of the formula (I) listed in Examples 1 or 2. Thereafter the fabric is rinsed and dried. After this treatment, the material shows an excellent brightening effect.

EXAMPLE 9

1 g of one of the compounds listed in Example 1 is incorporated into 1 kg of opaque plasticised polyvinyl chloride. The material then shows an excellent brightening effect and a clear white shade.

EXAMPLE 10

0.5 g of one of the compounds listed in Examples 1 and 2 is dissolved in 1 kg of a colourless lacquer of nitrocellulose or cellulose acetate. The lacquer is then spread thinly on a colourless base. After drying, the layer of lacquer shows an excellent brightening effect.

EXAMPLE 11

16.1 g of 3-[pyrazolyl-(1)]-7-[4-ethyl-5-methyl-v-triazolyl-(2)]-coumarine (compare Belgian Patent Specification No. 726,619, Example 1 d) in 250 ml of dichloroethane are treated dropwise, at 30°–35° C., with 8 g of sulphuryl chloride, whilst stirring. Thereafter the mixture is stirred for a further 3 hours at 50°–60° C., the solvent is then distilled off under reduced pressure, and the crude product which has separated out is recrystallised from chlorobenzene, using fuller's earth. 15 g of 3-[4-chloropyrazolyl-(1)]-7-[4-ethyl-5-methyl-v-triazolyl-(2)]-coumarine (compare Example 1b) are obtained as greenish-tinged white crystals which dissolve in dimethylformamide to give a strong reddish-tinged blue fluorescence.

We claim:

1. An optical brightener selected from the group consisting of

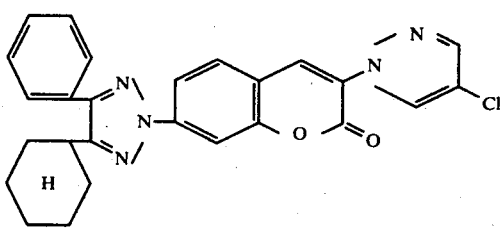

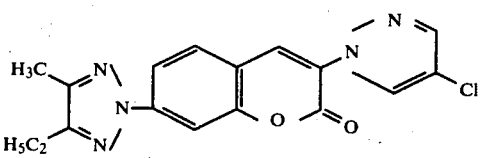

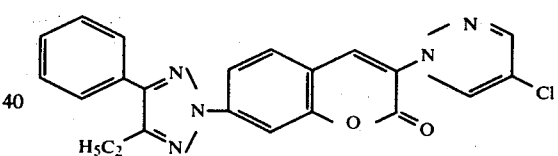

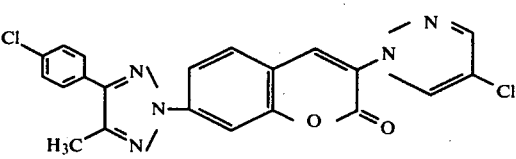

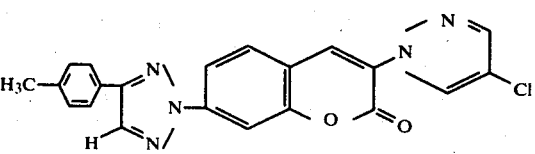

and

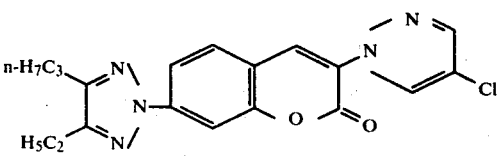

2. An optical brightener according to claim 1 of the formula

3. An optical brightener according to claim 1 of the formula
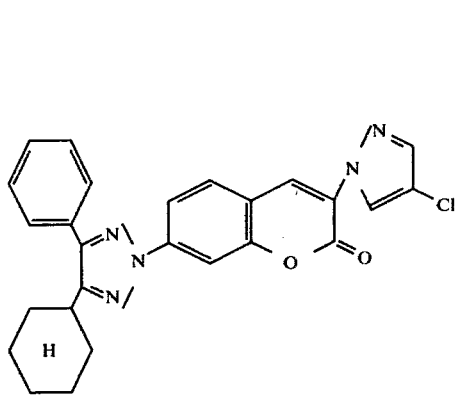
4. An optical brightener according to claim 1 of the formula
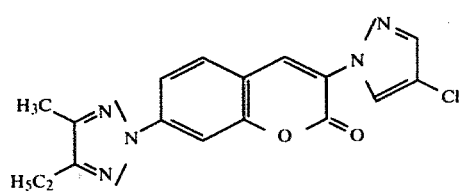
5. An optical brightener according to claim 1 of the formula
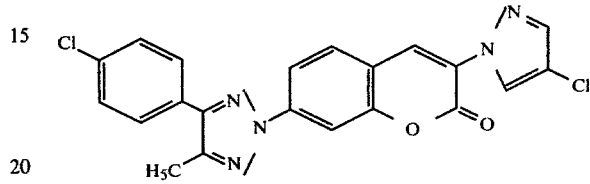
6. An optical brightener according to claim 1 of the formula
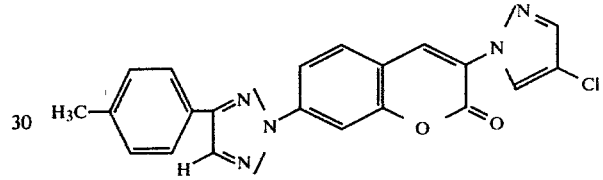
7. An optical brightener according to claim 1 of the formula
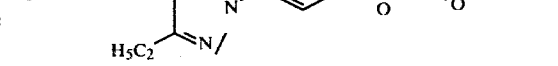
* * * * *

UNITED STATES PATENT AND TRADEMARK OFFICE
CERTIFICATE OF CORRECTION

PATENT NO. : 4,229,579
DATED : October 21, 1980
INVENTOR(S) : Alfons Dorlars et al It is certified that error appears in the above—identified patent and that said Letters Patent is hereby corrected as shown below:

Column 8, line 59, "triazlyl" should be "triazolyl".

Column 18, line 20, "$H_5C$" should be $H_3C$"

Signed and Sealed this

Sixteenth Day of June 1981

[SEAL]

Attest:

RENE D. TEGTMEYER

Attesting Officer     Acting Commissioner of Patents and Trademarks